US012714566B2

(12) United States Patent
Goswami

(10) Patent No.: US 12,714,566 B2
(45) Date of Patent: Aug. 25, 2026

(54) CARDIAC TREATMENT DEVICES AND METHODS

(71) Applicant: Mayo Foundation for Medical Education and Research, Rochester, MN (US)

(72) Inventor: Rohan M. Goswami, Jacksonville, FL (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 281 days.

(21) Appl. No.: 18/276,408

(22) PCT Filed: Feb. 22, 2022

(86) PCT No.: PCT/US2022/017267
§ 371 (c)(1),
(2) Date: Aug. 8, 2023

(87) PCT Pub. No.: WO2022/182637
PCT Pub. Date: Sep. 1, 2022

(65) Prior Publication Data

US 2024/0108468 A1 Apr. 4, 2024

Related U.S. Application Data

(60) Provisional application No. 63/152,594, filed on Feb. 23, 2021.

(51) Int. Cl.
*A61F 2/24* (2006.01)
*A61B 5/00* (2006.01)
(Continued)

(52) U.S. Cl.
CPC ............ *A61F 2/2487* (2013.01); *A61B 5/686* (2013.01); *A61N 1/3962* (2013.01);
(Continued)

(58) Field of Classification Search
CPC ............ A61F 2/2487; A61F 2002/0081; A61F 2210/0014; A61F 2220/0016; A61F 2230/0006; A61F 2230/0013; A61F 2230/0019; A61F 2230/0067; A61F 2250/0001; A61F 2250/0002; A61F 2250/0098; A61B 5/686; A61N 1/3962;
(Continued)

(56) References Cited

U.S. PATENT DOCUMENTS

2004/0002626 A1 1/2004 Feld et al.
2005/0015109 A1 1/2005 Lichtenstein
(Continued)

OTHER PUBLICATIONS

Partial Supplementary European Search Report in European Appln. No. 22760265.3, dated Aug. 26, 2024, 13 pages.
(Continued)

*Primary Examiner* — Jonathan T Kuo
(74) *Attorney, Agent, or Firm* — Fish & Richardson P.C.

(57) ABSTRACT

This document describes devices and methods for the treatment of heart conditions. For example, this document describes intraventricular implantable devices for treating heart failure. Such implantable devices offer the ability to augment cardiac function and allow potential myocardial recovery.

20 Claims, 16 Drawing Sheets

(51) Int. Cl.
*A61F 2/00* (2006.01)
*A61N 1/39* (2006.01)

(52) U.S. Cl.
CPC ................. *A61F 2002/0081* (2013.01); *A61F 2210/0014* (2013.01); *A61F 2220/0016* (2013.01); *A61F 2230/0006* (2013.01); *A61F 2230/0013* (2013.01); *A61F 2230/0019* (2013.01); *A61F 2230/0067* (2013.01); *A61F 2250/0001* (2013.01)

(58) Field of Classification Search
CPC .............. A61N 1/3627; A61N 1/36842; A61N 1/37518; A61N 1/37512; A61N 1/3756; A61N 1/37205; A61N 1/3787
See application file for complete search history.

(56) References Cited

U.S. PATENT DOCUMENTS

| | | | | |
|---|---|---|---|---|
| 2006/0025800 | A1* | 2/2006 | Suresh | A61F 2/2487 606/198 |
| 2006/0030881 | A1 | 2/2006 | Sharkey et al. | |
| 2014/0379041 | A1 | 12/2014 | Foster | |
| 2017/0290664 | A1 | 10/2017 | Alexander et al. | |

OTHER PUBLICATIONS

PCT International Search Report and Written Opinion in International Appln. No. PCT/US2022/017267, mailed on Jun. 27, 2022, 16 pages.

* cited by examiner

CARDIAC TREATMENT DEVICES AND METHODS

CROSS-REFERENCE TO RELATED APPLICATIONS

This application is a National Stage application under 35 U.S.C. § 371 of International Application No. PCT/US2022/017267, having an International Filing Date of Feb. 22, 2022, which claims the benefit of U.S. Provisional Application Ser. No. 63/152,594, filed Feb. 23, 2021. The disclosure of the prior application is considered part of (and is incorporated by reference in) the disclosure of this application.

BACKGROUND

1. Technical Field

This document relates to devices and methods for the treatment of heart conditions. For example, this document relates to intraventricular implantable devices for treating heart failure that offer the ability to augment systolic and diastolic (output and relaxation) cardiac function and allow potential myocardial recovery.

2. Background Information

The current treatment options for individuals with advanced cardiac dysfunction from a variety of reasons (e.g., heart attacks, chemotherapy, toxic exposure, hypertension, diabetes, viral infection, unknown familial genetic cause, etc.) are limited. Individuals may need durable support via implantation of an artificial heart pump (left ventricular assist device or "LVAD") as a bridge to transplantation or as destination (end of life) therapy. Other individuals not undergoing implantation of an artificial heart pump may require the continuous infusion of intravenous medications to support failing heart function lifelong.

Currently, there are no intraventricular implantable devices that offer the ability to augment cardiac function and allow potential myocardial recovery or support as bridge to transplantation. Although attempts have been made to create devices to augment cardiac contraction, these devices have been surgically implanted and are not durable due to the need for external power supplies and associated complications including infection, bleeding, stroke or formation of blood clots.

SUMMARY

This document describes devices and methods for the treatment of heart conditions. For example, this document describes intraventricular implantable devices for treating heart failure that offer the ability to augment cardiac function and allow potential myocardial recovery.

In one aspect, this disclosure is directed to an intraventricular implantable device that is configured to augment cardiac function. The intraventricular implantable device includes a framework, multiple anchor nodes, and an apical cone. The framework includes multiple elongate Nitinol wires arranged in a conical shape that defines a central longitudinal axis. The multiple elongate Nitinol wires include: (i) multiple longitudinally-extending Nitinol wires extending from an apex of the conical shape to a base termination end located opposite of the apex and (ii) multiple circumferentially-extending Nitinol wires disposed at multiple locations along the central longitudinal axis. The multiple anchor nodes interconnect intersections of the multiple longitudinally-extending Nitinol wires with the multiple circumferentially-extending Nitinol wires. The apical cone is attached to the multiple longitudinally-extending Nitinol wires at the apex of the conical shape.

Such an intraventricular implantable device may optionally include one or more of the following features. In some embodiments, at least some of the multiple longitudinally-extending Nitinol wires and at least some of the multiple circumferentially-extending Nitinol wires extend along undulating paths. The apical cone may define an internal space that contains electronics. In some embodiments, the electronics comprise a wireless communications transmitter or transceiver. In some example embodiments, the electronics comprise one or more capacitors configured for storing electrical energy. The device may be configured to deliver the electrical energy as a pacemaker or for defibrillation. In some embodiments, the device does not require a battery power supply to function. At least some of the anchor nodes may include sensors to monitor hemodynamics, blood lab values, or to provide electrical detection of heart rhythm.

In another aspect, this disclosure is directed to a method of treating heart failure of a patient. The method includes implanting the intraventricular implantable device described herein in a ventricle of the patient. The implanted intraventricular implantable device may include any of the optional features described herein. The ventricle may be a right ventricle of the patient, or a left ventricle of the patient.

Particular embodiments of the subject matter described in this document can be implemented to realize one or more of the following advantages. First, the devices described herein decrease the total work needed to generate a basal force required to contract the ventricle within which the device is placed.

Second, the devices described herein are deliverable within the left and/or right ventricle. Presently, there is no similar device designed for permanent implantation in the right ventricle.

Third, the devices described herein do not require a power supply (e.g., battery) to function. Rather, the devices described herein are designed to improve heart function by augmentation of the natural contractile force of the heart.

Fourth, the devices described herein include the ability to utilize the kinetic battery to power secondary functions of the device. Such secondary functions may include, but are not limited to, monitoring hemodynamics, blood lab values, providing electrical detection of heart rhythms, and delivering stimulation as a pacemaker or for defibrillation.

Fifth, in some embodiments heart conditions such as heart failure and others can be treated using the devices and methods provided herein. In some embodiments, various heart conditions can be treated in a minimally invasive fashion using the devices and methods provided herein. Such minimally invasive techniques can reduce recovery times, patient discomfort, and treatment costs.

Sixth, in some embodiments the devices described herein include a modular design that is scalable to ventricular dimensions to meet needs of specific use-case scenarios, or to the generalized predictable nature of heart failure progression.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

Like reference numbers represent corresponding parts throughout.

DETAILED DESCRIPTION

This document describes devices and methods for the treatment of heart conditions. For example, this document describes implantable intraventricular tensile myocardial recovery devices ("IMRDs", or "IMRD" singularly) for treating heart failure. As described further below, the IMRDs offer the ability to augment cardiac function (output) and to allow potential myocardial recovery.

The IMRDs described herein are designed to perform a variety of functions that allow the devices to both positively augment the generated force from within a hollow chamber (e.g., ventricle) as well as evenly distribute the tension of said force within the ventricle it is placed. The use of the IMRDs decrease the total work needed to generate a basal force required to contract the ventricle within which it is placed. The IMRDs also assist in evenly distributing forces of relaxation within the ventricle it is placed.

The IMRDs described herein provide a new solution to myocardial recovery technology. The IMRDs are designed to operate in the absence of an electrical power source (e.g., no battery is needed). The structure of the IMRDs allows for peripheral, minimally invasive, implantation through the femoral or axillary arteries rather than open-heart surgery and heart-lung machine support.

When implanted within a heart ventricle, the IMRDs will expand to rest within the ventricular cavity from apex to base. As a result of implantation, the myocardial wall stress will directly drive the augmented force of contraction (using the law of LaPlace and the force tension relationship between a spherical shape). This potential energy will be converted to kinetic energy, as the IMRD always wants to return to its contracted state. The IMRDs can be customized to an individual's specific ventricular chamber size. This will provide further augmentation based on the individually determined ventricular geometry and improve the transfer of energy.

Figure 1:
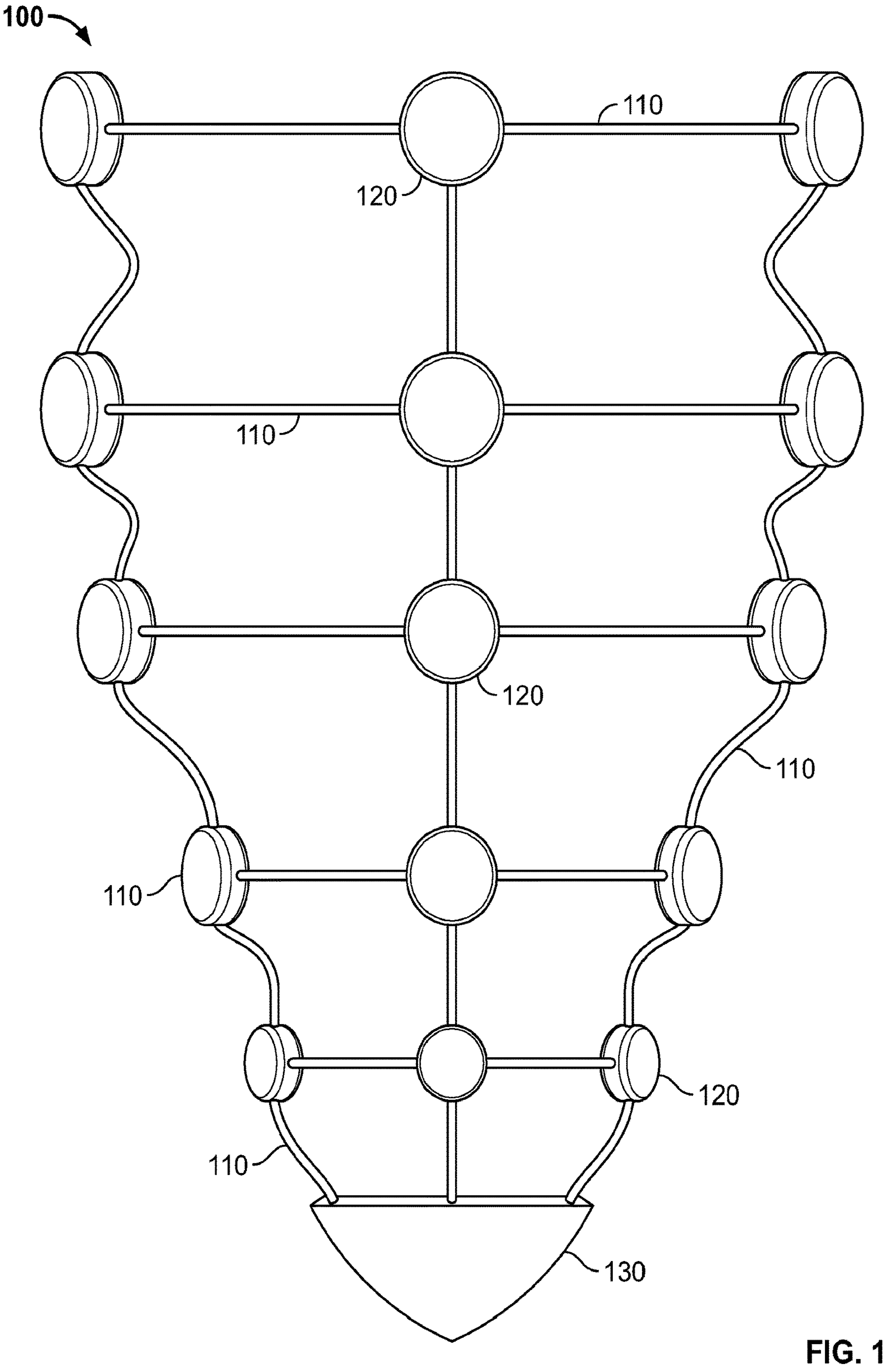
FIG. 1 is side view of an example implantable intraventricular tensile myocardial recovery device in accordance with some embodiments provided herein.
Figure 2:
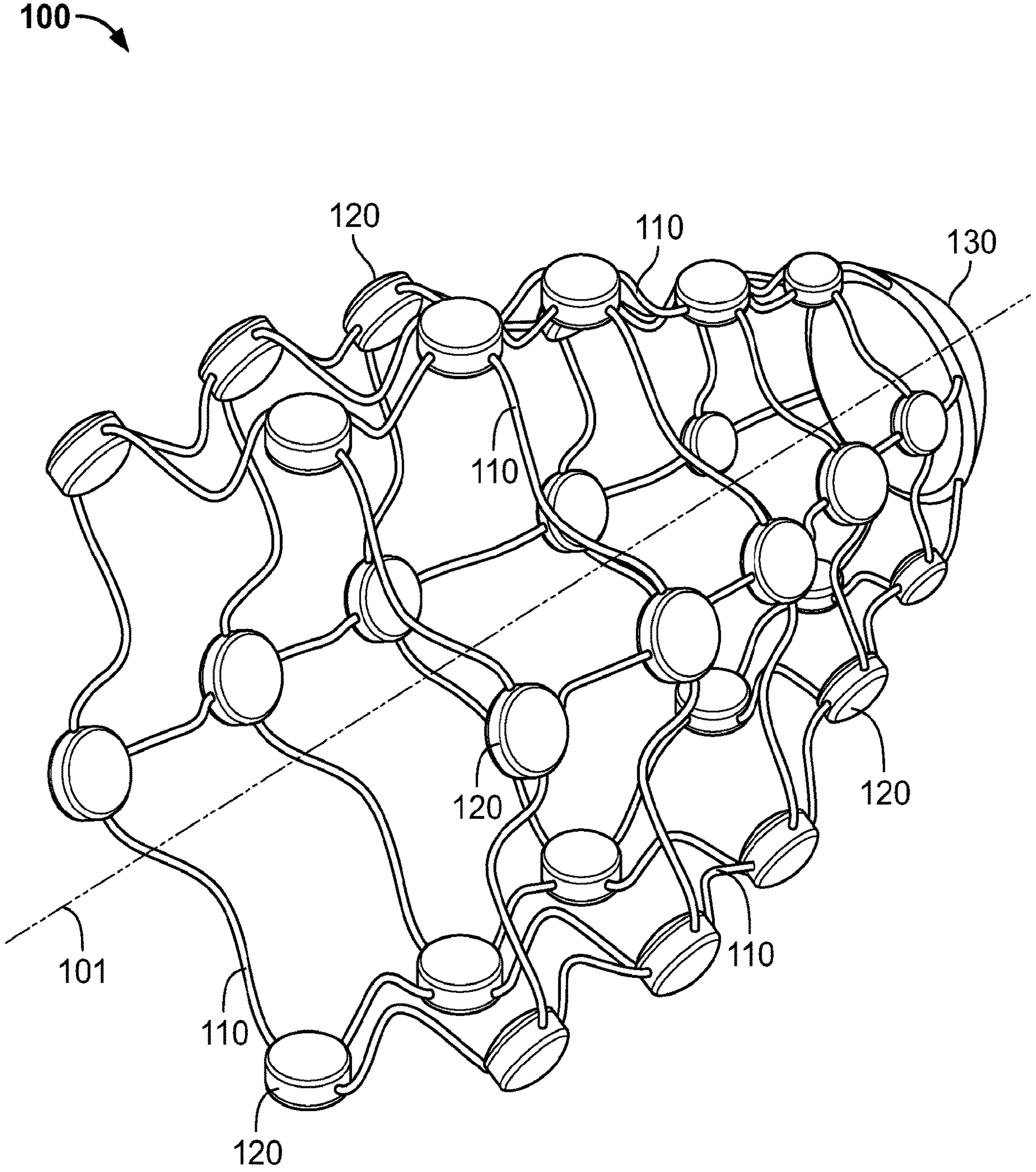
FIG. 2 is a perspective view of the implantable intraventricular tensile myocardial recovery device of FIG. 1.
Figure 3:
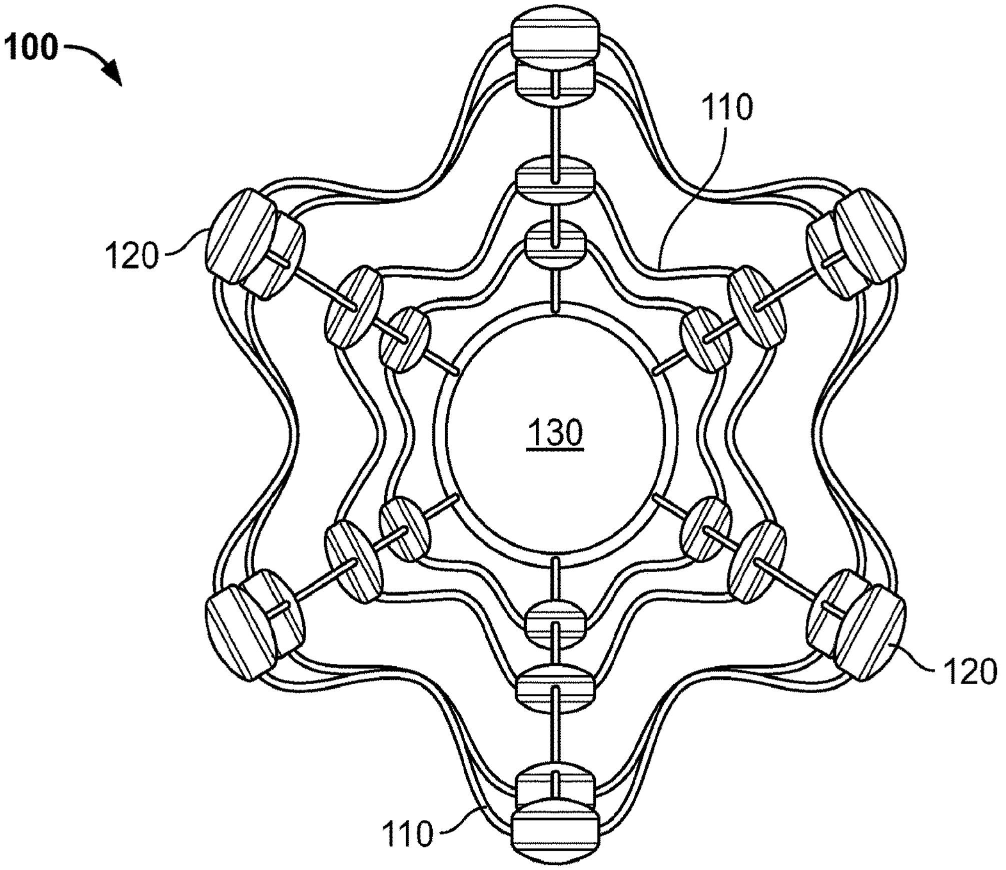
FIG. 3 is an end view of the implantable intraventricular tensile myocardial recovery device of FIG. 1.

Referring to FIGS. 1-3, an example IMRD 100 can be configured for implantation within a patient's ventricle (right or left) using a minimally invasive approach. The IMRD 100 is constructed with temperature-sensitive materials such that the IMRD 100 has an enlarged configuration (e.g., FIGS. 1-3) when its temperature is above a transition temperature, and a contracted configuration (e.g., FIG. 4) when its temperature is below the transition temperature. This temperature-responsive reconfiguration characteristic of the IMRD 100 is used to augment the force of contraction of the ventricle in which the IMRD 100 is residing. Accordingly, the output of the ventricle is increased by virtue of the IMRD 100.

The construct of the depicted example IMRD 100 includes a framework 110, anchor nodes 120, and an apical cone 130. The framework 110 includes multiple individual elongate members. Some of the elongate members of the framework 110 extend longitudinally (as defined by the longitudinal axis 101, FIG. 2). Other elongate members of the framework 110 extend circumferentially around the longitudinal axis 101. The outer profile of the framework 110 is generally conical.

The anchor nodes 120 are attached to the elongate members of the framework 110 at the junctions of the longitudinally-extending and the circumferentially-extending elongate members. The anchor nodes 120 serve to capture and interconnect those elongate members to make the framework 110 a unitary construct.

The apical cone 130 is located at an end of the IMRD 100. The longitudinally-extending elongate members of the framework 110 attach to the apical cone 130.

Now that the general construction of the IMRD 100 has been described, more details will be provided about each of the aforementioned components.

First, the framework 110 is comprised of multiple elongate members that can also be considered to be "wires." The wires can have circular cross-sectional shapes, square, polygonal, oblong, or any other desired cross-sectional shape, and combinations thereof. For example, in some embodiments the longitudinally-extending elongate members are different than the circumferentially-extending elongate members. In some embodiments, they are the same. This framework 110 increases in diameter from the apical cone 130 to the opposite base termination end.

The wires of the framework 110 extend along undulating paths (also like a wave-form with multiple peaks and valleys). For example, the circumferentially-extending wires do not form a perfect circle. Instead, the undulations of the circumferentially-extending wires create a star-like shape. In addition, the undulations of the longitudinally-extending wires cause the conical outer profile to vary in diameter along its longitudinal direction, from larger in diameter to smaller in diameter—to larger in diameter to smaller in diameter—to larger in diameter to smaller in diameter, and so on, along the longitudinal length of the framework 110.

Figure 4:
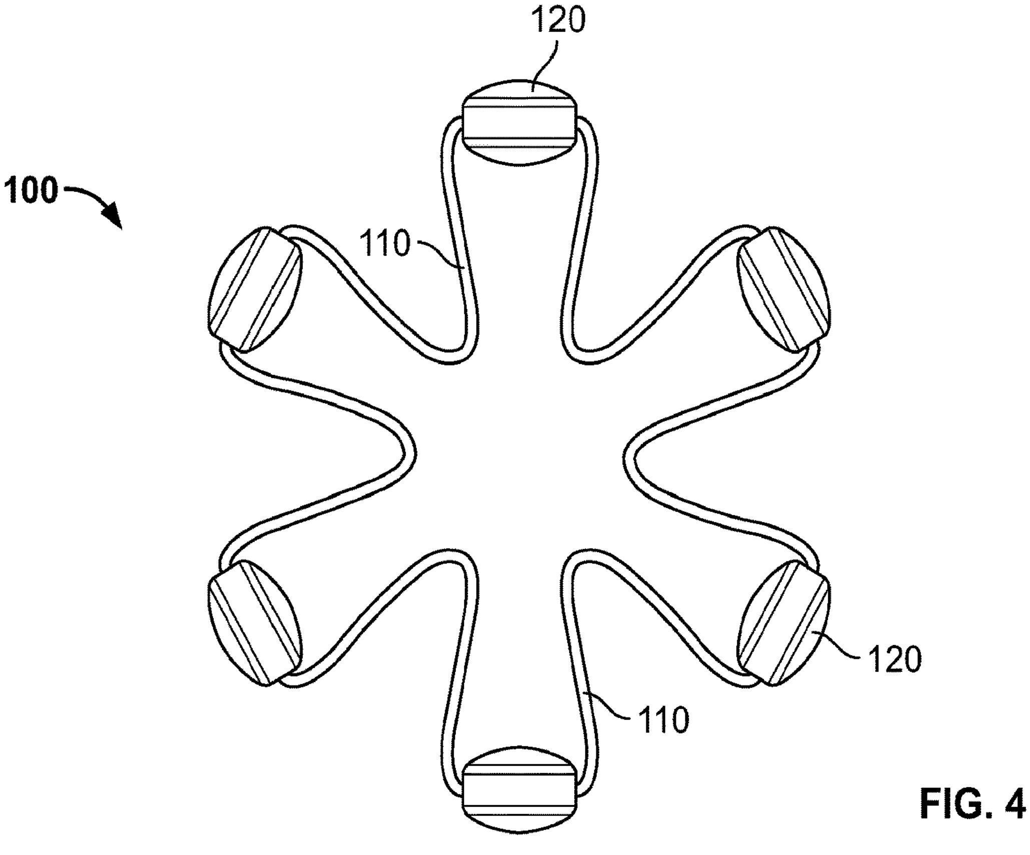
FIG. 4 is an end view of the implantable intraventricular tensile myocardial recovery device of FIG. 1 in a contracted configuration.

In some embodiments, the wires of the framework 110 are made of Nitinol. Nitinol is a nickel-titanium alloy with super elasticity and shape memory properties. Shape memory refers to the ability of Nitinol to undergo deformation at one temperature, and then to recover its original shape upon heating above its transformation temperature. This temperature-dependent transformation property is used for the functionality of the IMRD 100, as described further below. The original shape of the IMRD 100 is depicted in FIGS. 1-3. The deformed shape of the IMRD 100 is depicted in FIG. 4, as described further below.

Each wire portion of the framework 110 is heat shape-set to a manufactured specific diameter for generalized use within the ventricle it is placed into. Each wire member of the framework 110, when attached together by the anchor nodes 120 is designed to collapse onto itself when force applied is exerted on the anchor nodes 120, and reversely true, is the need for the IMRD 100 to expand to its preconfigured shape when reaching maximal nadir of contraction.

Figure 6:
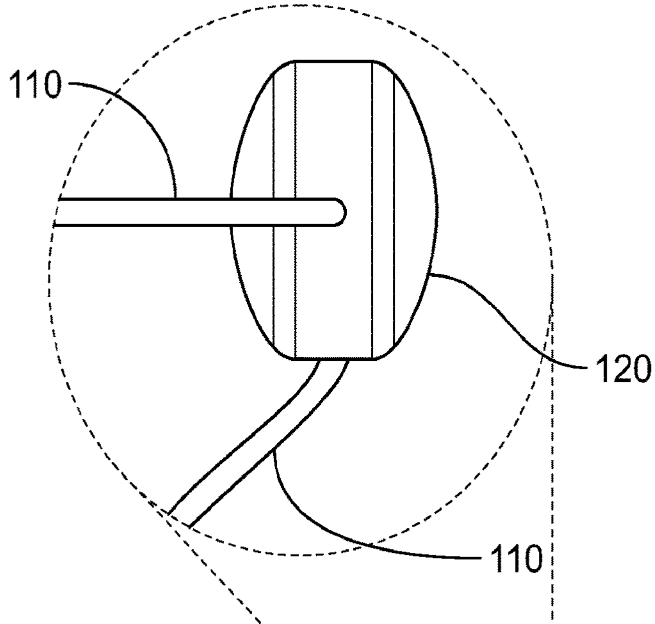
FIG. 6 is an enlarged view of an anchor node of the implantable intraventricular tensile myocardial recovery device of FIG. 1.
Figure 5:
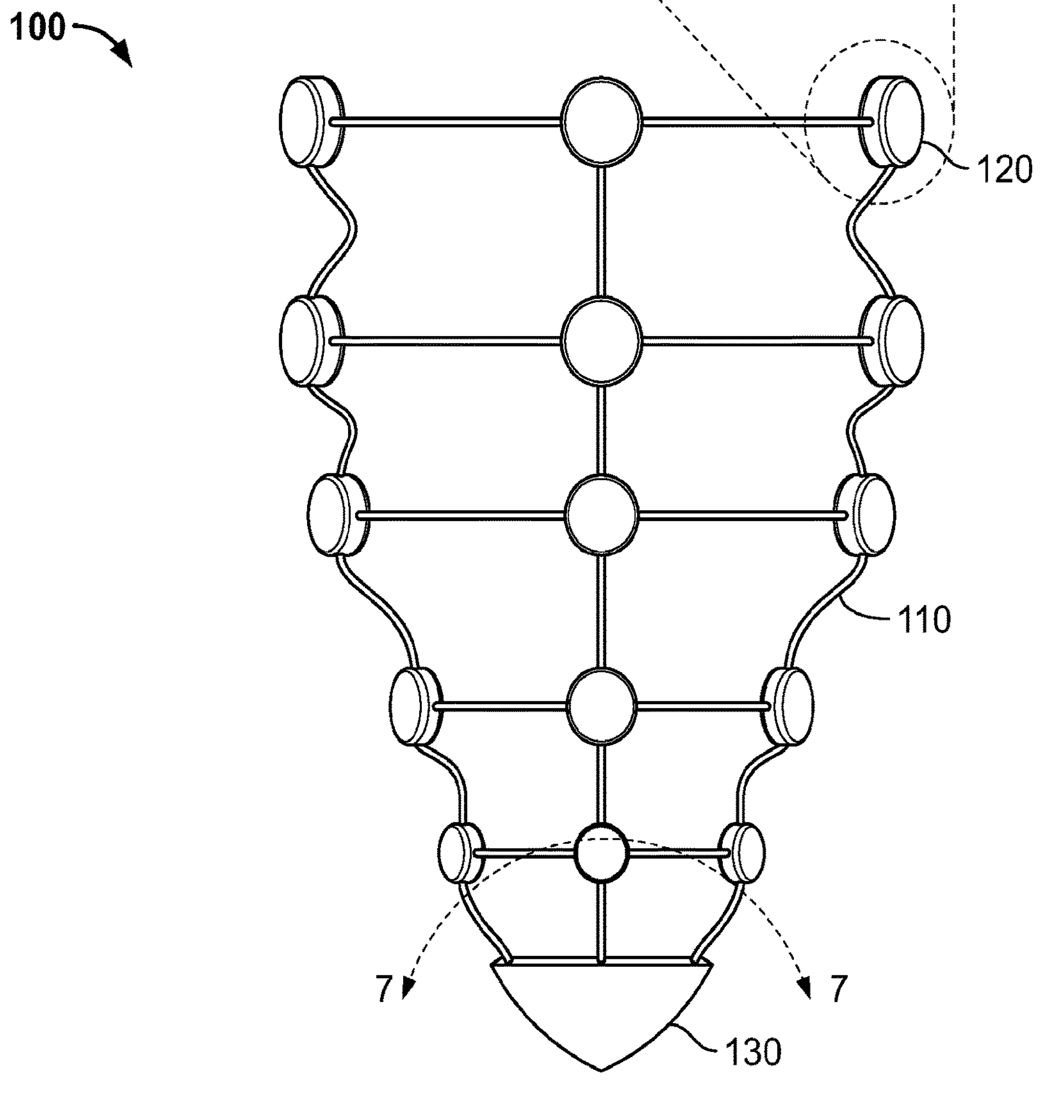
FIG. 5 is a side view of the implantable intraventricular tensile myocardial recovery device of FIG. 1.

Next, also referring to FIGS. 5 and 6, the anchor nodes 120 are configured to facilitate equal distribution of circumferential, horizontal and vertical shear stresses as they optimize force generation. Each anchor node 120 is form-molded to contain one or more wires of the framework 110 so as to make the anchor nodes 120 a structural point within the IMRD 100 that increases the overall strength of the IMRD 100.

In addition, the anchor nodes 120 are configured to attach to the inner wall of the ventricle. In some embodiments, the anchor nodes 120 are coated (e.g., on the radially outward facing surfaces) with a bioactive steroid polymer (e.g., pacemaker glue) which is standard for biological applications of such devices. They can be shaped or contoured in order to increase surface area for attachment to the ventricular wall.

Furthermore, in some embodiments particular anchor nodes 120 may be specifically marked for orientation purposes and/or fitted with internal circuitry or electrical components that may be utilized for conduction of electrical current or measurement via sensor technologies. For example, in some embodiments the particular anchor nodes 120 can contain microcircuit arrays and/or communications technologies to monitor blood work on a continuous format basis, pressures, motion, and other properties. In some embodiments, particular anchor nodes 120 can be used to deliver pacing, or for defibrillation energy delivery.

In some embodiments, certain anchor nodes 120 may include radiopaque properties so that the rotary position of the IMRD 100 may be radiographically viewed. This functionality can be used to ensure avoidance of leaflet and/or chordae interference.

Figure 7:
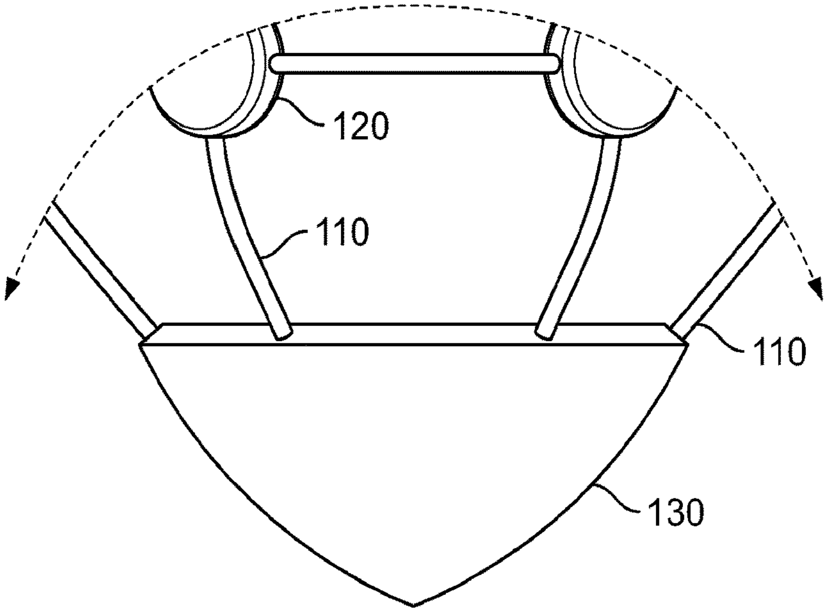
FIG. 7 is an enlarged view of an apical cone of the implantable intraventricular tensile myocardial recovery device of FIG. 1.

Next, also referring to FIGS. 5 and 7, the apical termination of the IMRD 100 occurs with a molded or formed cone structure referred to herein as the apical cone 130. The structure of the apical cone 130 provides both a large surface area for adhesion and placement of the device within the apex of the ventricular chamber it is placed into.

Figure 8:
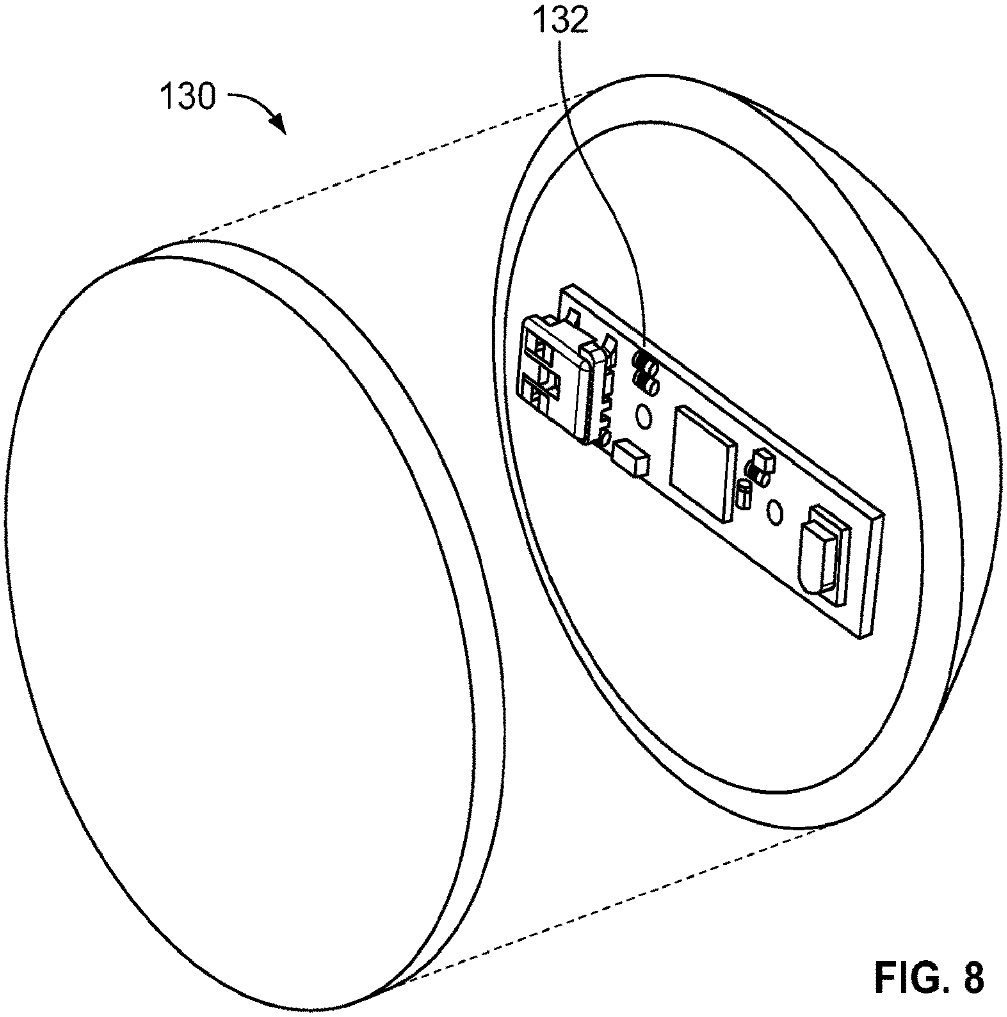
FIG. 8 is an exploded perspective view of the apical cone of FIG. 7.

Furthermore, as shown in FIG. 8, the apical cone 130 is a multi-purpose structure that defines an internal space that can house various types of multiple-use technologies 132 based upon the device's functional need (e.g., electrical capacitor(s), biological sensors, circuit boards, wireless transceiver, etc.) that allow customization of the device without need for significant structural impact.

In some embodiments, the multiple-use technologies 132 can include one or more IoT devices. The multiple-use technologies 132 can also include one or more devices for wireless communications such as, but not limited to, Bluetooth®, ultra-wide band, and/or near field communications.

In some embodiments, the kinetic motion of the heart can be harnessed by the IMRD 100 to generate power that can be stored in one or more capacitors located in the apical cone 130.

Figure 9:
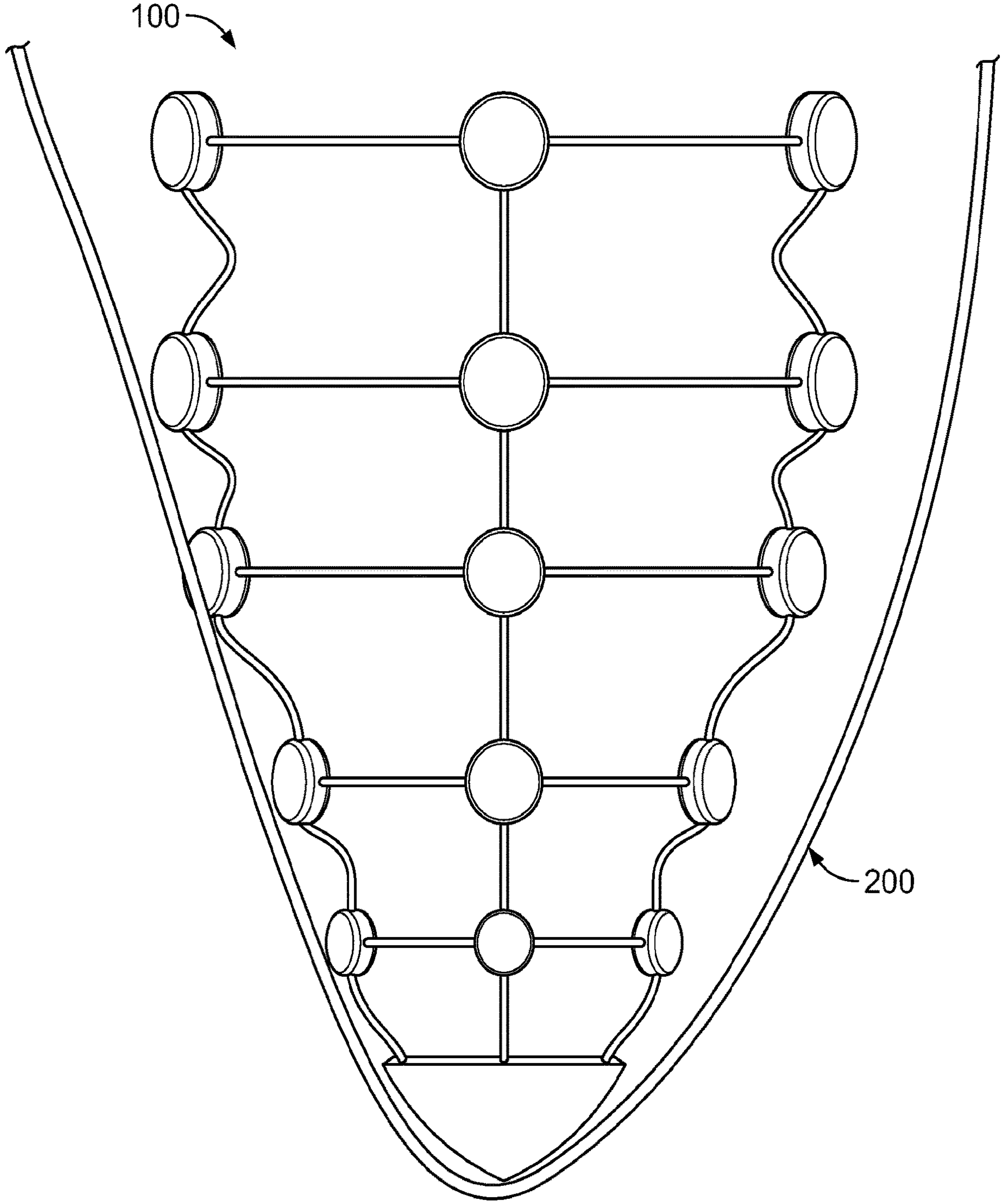
FIG. 9 shows the implantable intraventricular tensile myocardial recovery device of FIG. 1 within a ventricle during diastole.

Referring to FIG. 9, the IMRD 100 is depicted in a ventricle 200 that is in a relaxed state (at the beginning of diastole). In this state, the Nitinol framework 110 of the IMRD 100 is above its transformation temperature.

Figure 10:
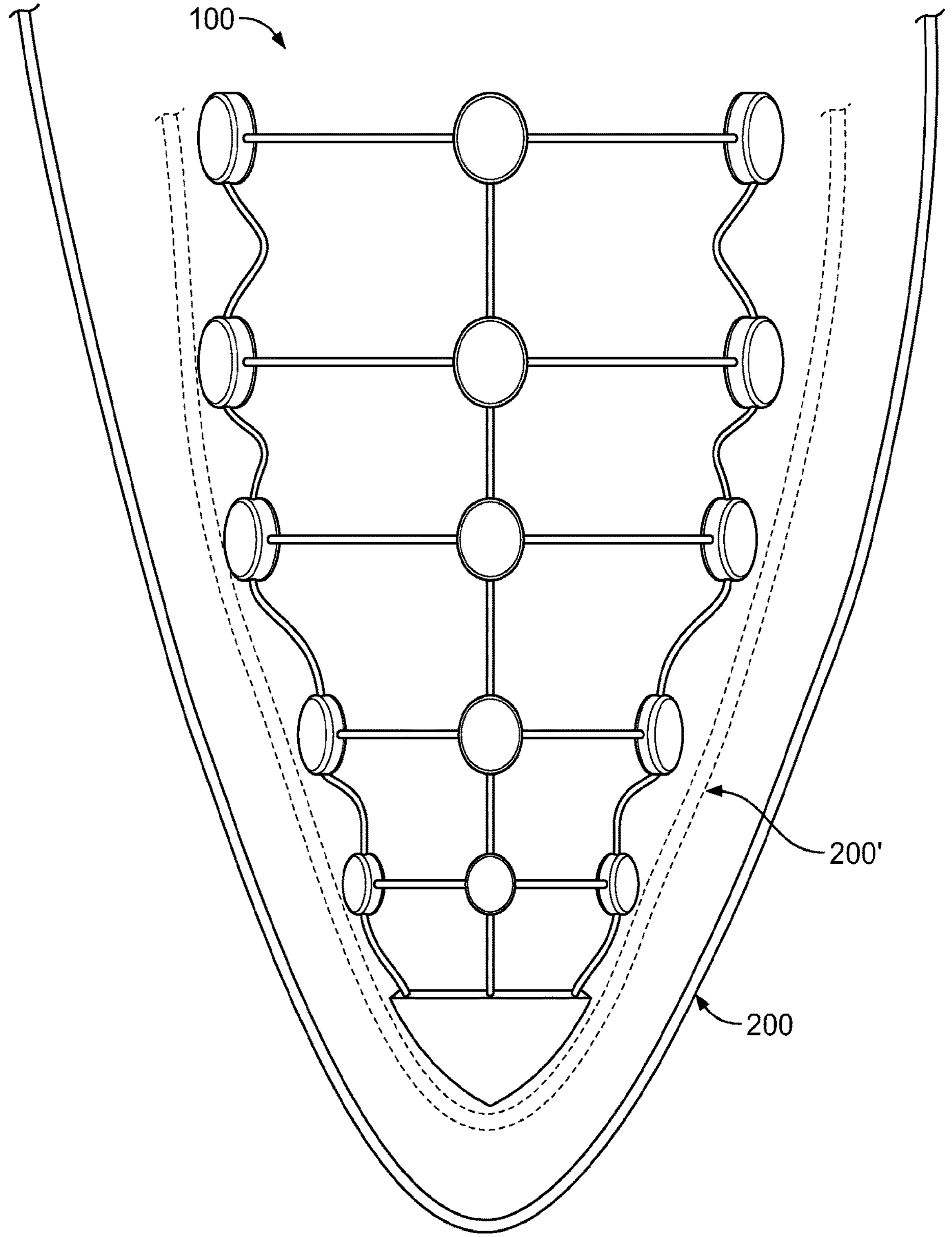
FIG. 10 shows the implantable intraventricular tensile myocardial recovery device of FIG. 1 within a ventricle during systole. The solid outer line shows the contraction of the ventricle without the assistance of the device, and the inner dashed line shows the contraction of the ventricle with the assistance of the device.

Referring to FIGS. 4 and 10, during diastole blood rushes into the ventricle. When that happens, the blood cools the Nitinol framework 110 of the IMRD 100 to below its transformation temperature. In response to the cooling of the Nitinol framework 110, the IMRD 100 physically contracts in three dimensions. For example, the contraction of the framework 110 causes the IMRD 100 to radially contract (FIG. 4), to longitudinally contract, and to rotationally twist. The extent of these motions can be controlled by the shape of the wires of the Nitinol framework 110. For example, in some embodiments the diameter of the IMRD 100 when it is above its transformation temperature is about 6 cm in diameter, and when the IMRD 100 is below its transformation temperature is about 3 to 5 cm in diameter.

FIG. 10 shows the augmentation effect of the IMRD 100. That is, the outer solid line depicts the wall of the ventricle without the augmentation of the IMRD 100. In comparison, the inner dashed line depicts the wall of the ventricle with the augmentation of the IMRD 100. It can be envisioned that the use of the IMRD 100 causes heart function to improve by increasing cardiac output from the ventricle because the ventricle is caused to contract farther than without the use of the IMRD 100. The Nitinol framework 110 acts as a kinetic agent to augment the pumping force of the heart.

The IMRDs described herein augment the contraction and relaxation phases of the heart during each heartbeat. In some embodiments, the IMRDs described herein function by utilizing the stored potential energy in the native heart muscle.

In patients with cardiomyopathy or 'weakened heart muscles' their constellation of symptoms is due to inability to deliver oxygenated blood to end organs as well as increased pressure within the four chambers of the heart. This results in a cascade of downstream effects on the kidneys, liver and blood vessel systems through hormone release and lack of adequate blood flow.

The IMRDs described herein have been developed to optimize heart function, while at the same time, allowing implantation in nearly all heart failure patients—regardless of the cause of the heart failure. To simply describe the benefit of this device, for example: if a patient with heart failure has an ejection fraction of 20% (normal being >=50%) the average amount of blood ejected to the body each beat is around 50 cc, at a heart rate of 80 beats per minute that yields a total cardiac output of 4 liters per minute. (normal being >4 L/min). With the IMRD, an augmentation of contraction by optimizing muscle contraction of just 10 cc per beat will increase the patient's effective cardiac output to 4.8 L/min—or normalize the heart function with very little overall change in cardiac mechanics. This is the novel approach to improving patient's quality of life and organ function—augmenting a minor amount of cardiac function in order to yield an exponential change with maximal benefits. As such, this device would allow patients not candidates for LVAD therapy or heart transplantation the potential for increased quality and quantity of life by receiving this treatment, improving daily functional capacity and symptom relief—all the while reducing the traditional risk of complications such as stroke or infection/rejection innate to LVAD and transplantation, respectively.

Furthermore, the repeated contraction/expansion function of the IMRDs substructure is what allows for the natural generation of increased transference of force—by continually working to maintain its collapsed shape, it allows for augmentation of the ventricle it is placed into by decreasing net work performed by each individual component and distributes this work in order to improve the force-tension relationship and decrease net energy expenditure. Actuation of the IMRDs occurs through active forces generated by the ventricle it is placed into, and subsequently augments pumping by the method described above.

During systole: The IMRD is augmenting the ventricle closure. The IMRD is transferring energy from the heart.

During diastole: As the ventricle is recoiling back, the IMRD returns to its larger normal shape. Energy is now transferred back to the heart.

The following is a list of some additional benefits provided by the IMRDs described herein: (i) Decreases the intrinsic energy requirements of the ventricle it is placed in; (ii) Optimizes volume unloading by augmenting systolic contraction; (iii) Independent of baseline cardiac disorder; and (iv) Modular design is scalable to ventricular dimensions to meet needs of specific use-case scenarios or to the generalized predictable nature of heart failure progression.

Multiple embodiments of the IMRDs described herein are possible, without limitation. For example: (i) Solely basic implantable framework device (Left or Right ventricle placement); (ii) Basic implantable device plus an apical cone pressure sensor and wireless communication capabilities (e.g., a NFC transmitter); or (iii) Monitored implantable device plus real-time multi-sensor array with advanced capabilities.

Moreover, the described herein include the ability to harness the kinetic of the heart to power secondary functions of the IMRDs that may include, but are not limited to, monitoring hemodynamics, blood lab values, and providing electrical detection of heart rhythm and delivering stimulation as a pacemaker or for defibrillation.

Deployment of the IMRDs described herein device is detailed below as a novel method to allow for repositioning, maintenance of a blood-device barrier and application of targeted delivery in a percutaneous fashion.

In some embodiments, the deployment system is comprised of:

1. Outer sheath
2. Air buffer
3. Inner sheath
4. Outer sheath control system
5. 3-Way stop-cock for air retrieval
6. Radiopaque positional marker
7. Radiopaque deployment marker
8. Outer sheath arterial pressure monitoring catheter
9. Outer sheath pressure monitoring one-way system The above deployment system is designed to allow for novel functions including, but not limited to:

1. Blood-free delivery of the device within the human body, specifically the left or right ventricle, while maintaining a blood-device barrier through the use of a dual sheath system and air buffer. This system allows the placement of the device within an inner sheath that is surrounded by a thin layer of air (e.g., about 4 cc in some embodiments, without limitation), allowing for optimal temperature control as well as device stability.
2. As the device is placed within the femoral or subclavian artery or femoral or internal jugular vein, it is advanced under fluoroscopic guidance within the arterial or venous systems and tracked with the distal marker. The device controls are maintained by both the outer sheath and control system.
3. In some embodiments, the outer sheath control system is designed to allow for a 26-45 degree bend (predetermined left/right femoral or left/right axillary or left/right internal jugular). This z-plane movement allows for adequate placement within the left ventricle over a stiff guide wire, monorail system with pinpoint control of the distal end of the device tip.
4. The inner sheath is specifically designed to allow for placement and repositioning, and protection of the device until deployment. This sheath utilizes the air buffer as a lubricant to allow the sheath to move independently when being deployed and positioned in relation to the outer sheath. Once the inner and outer sheaths are separated from each other, as the outer sheath is pulled back, the device is no longer retrievable. It remains positionable.

Figure 11:
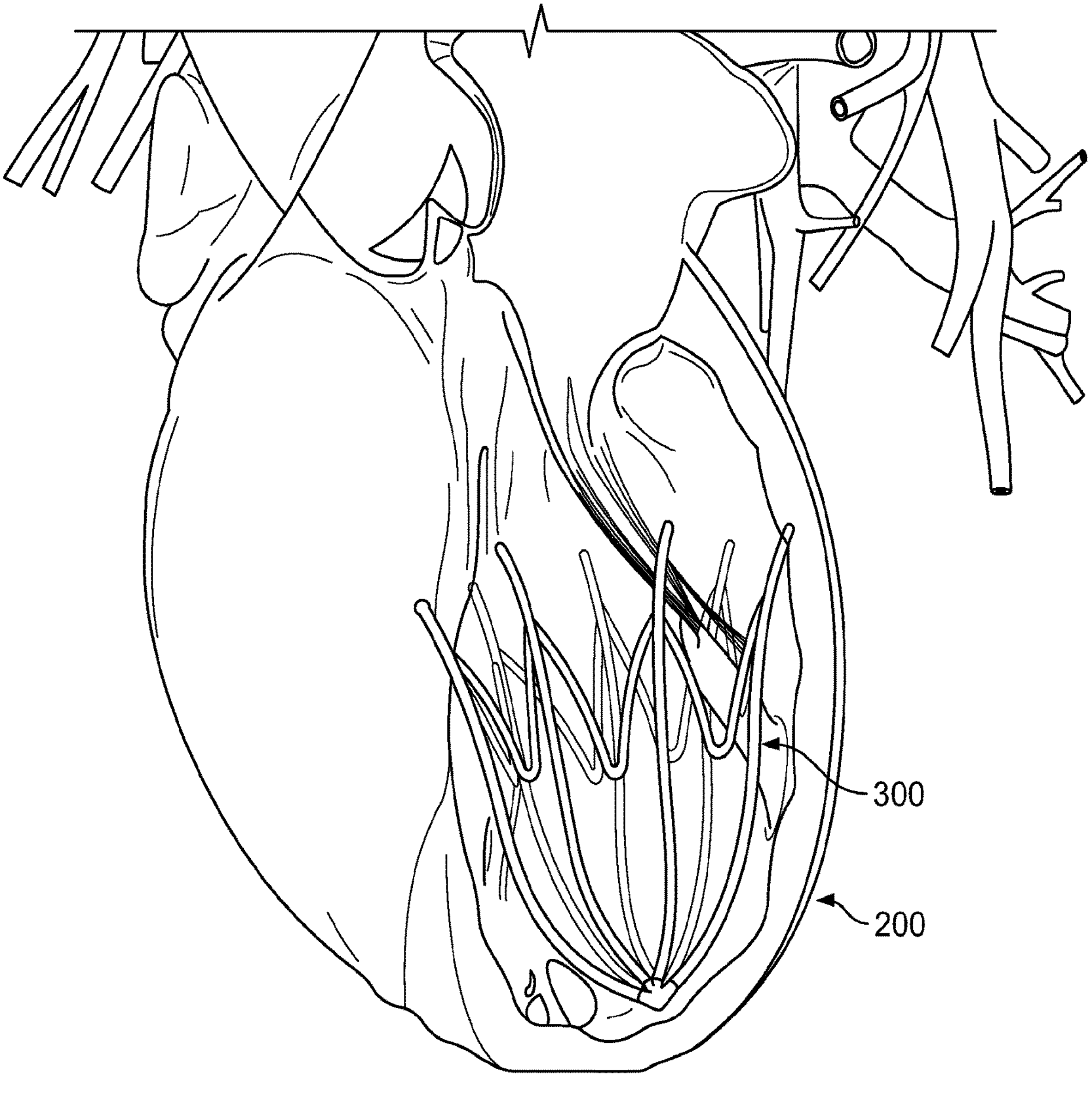
FIG. 11 depicts an example implantable intraventricular tensile myocardial recovery device within a ventricle of a heart.

FIG. 11 depicts another example type of IMRD 300 that is implanted within the ventricle 200. The IMRD 300 can be said to resemble the shape of a tulip. As described above, the IMRD 300 augments the contraction and relaxation phases of the heart (e.g., the ventricle 200) during each heartbeat. Accordingly, the IMRD 300 can be used to treat heart failure (such as dilated cardiomyopathy in the human heart left ventricle). The IMRD 300 can be provided in multiple sizes to support the treatment of a range of patients.

Figure 12:
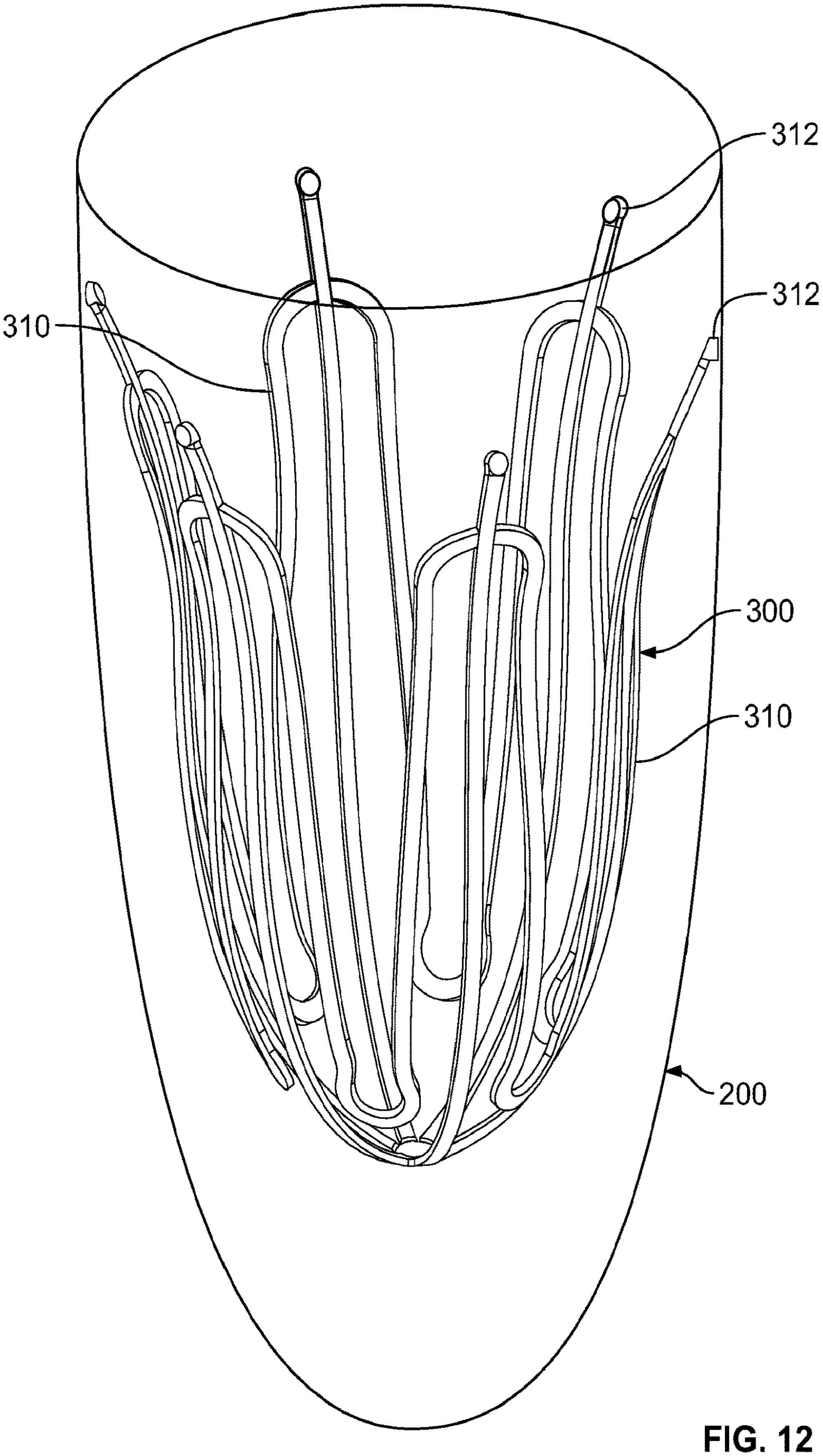
FIG. 12 is an enlarged view of the implantable intraventricular tensile myocardial recovery device of FIG. 11 within a schematically represented ventricle.

FIG. 12 is another view of the IMRD 300 within the left ventricle 200. The IMRD 300 includes a Nitinol framework 310. The Nitinol framework 310 is a flexible structure that limits the expansion of the left ventricle 200 to prevent over-expansion. Additionally, the Nitinol framework 310 augments patient's heart by storing energy during heart expansion (diastole) and releasing stored energy during heart contraction (systole). The Nitinol framework 310 is designed to flex for the lifetime of the patient (e.g., billions of cycles).

The Nitinol framework 310 has superelasticity and shape memory properties. That means the Nitinol framework 310 can remember its original shape and return to it when heated. The Nitinol framework 310 also shows great elasticity under stress. Accordingly, the IMRD 300 can be radially compressed to a very low profile for transcatheter delivery to the ventricle 200. The Nitinol framework 310 can self-expand to the illustrated configuration when it emerges from a delivery sheath/catheter.

The Nitinol framework 310 can include various types of physical features for anchoring the IMRD 300 to the ventricle 200, and to thereby provide migration resistance. For example, in the depicted embodiment the framework 310 includes integrated attachment barbs 312 that are used to secure the IMRD 300 within the wall of the ventricle 200. In some cases, the attachment barbs 312 are inserted into the heart wall during initial the insertion of the IMRD 300 within the ventricle 200. The attachment barbs 312 can induce heart wall tissue ingrowth, for additional securing and migration resistance.

Figure 13:
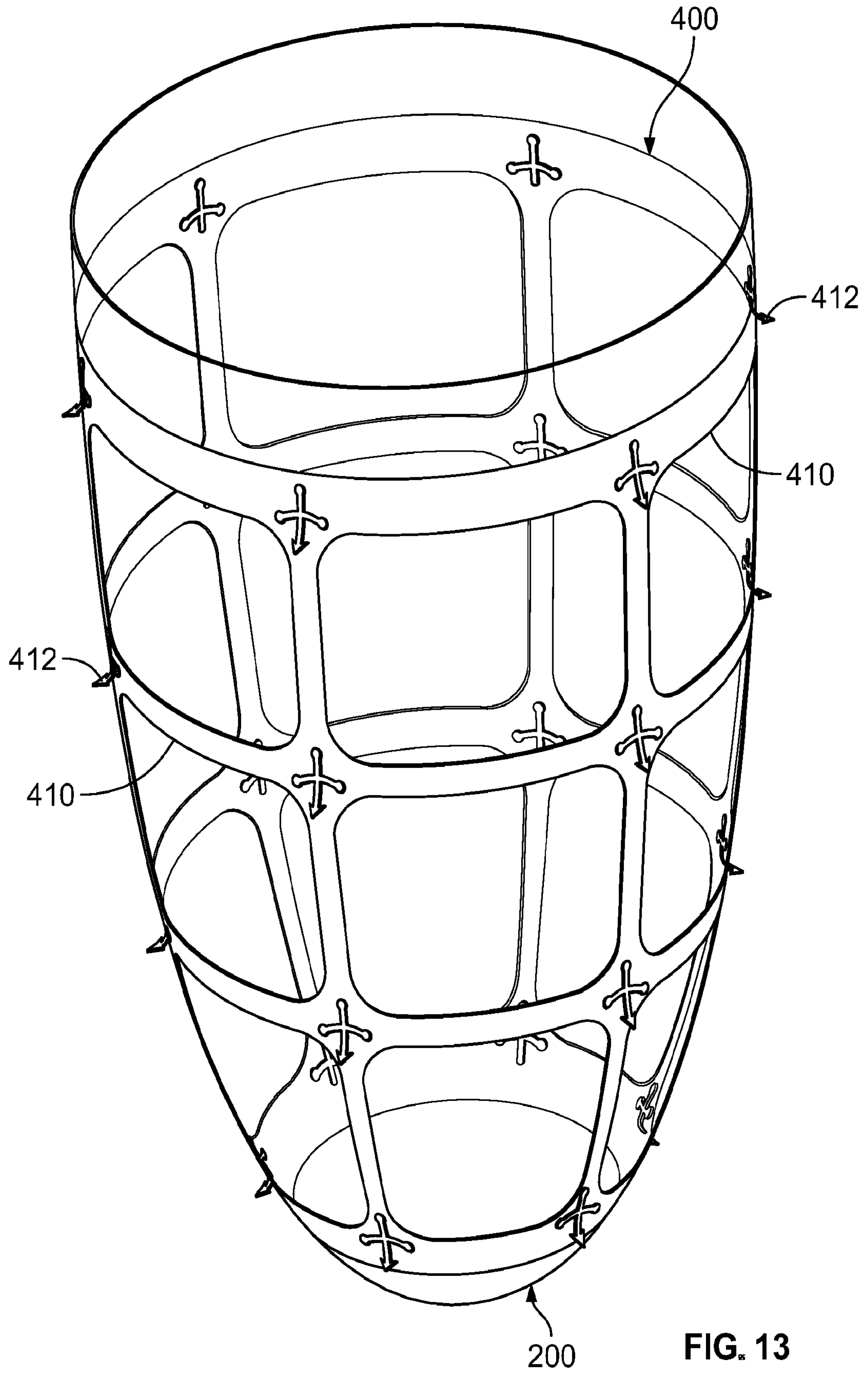
FIG. 13 is an enlarged view of another example implantable intraventricular tensile myocardial recovery device within a schematically represented ventricle.

FIG. 13 depicts another example type of IMRD 400 that is configured to be implanted within the ventricle 200. The IMRD 400 includes a lattice structure 410. The lattice structure 410 is a flexible structure that limits the expansion of the left ventricle 200 to prevent over-expansion. Additionally, the lattice structure 410 augments the patient's heart by storing energy during heart expansion (diastole) and releasing stored energy during heart contraction (systole). The lattice structure 410 can collapse freely during systole. The lattice structure 410 is designed to flex for the lifetime of the patient (e.g., billions of cycles).

In some embodiments, the lattice structure 410 is comprised of a fabric material such as, but not limited to, polyester. For example, in some embodiments the fabric material is polyester configured in a woven or knit construction. One of the benefits provided by using such a fabric as a material of the lattice structure 410 is fatigue resistance. That is, in some embodiments the lattice structure 410 comprised of a fabric material will last longer than other types of materials.

The lattice structure 410 is comprised of multiple rectangular cells that arranged into a generally cylindrical or frustoconical shape. Other polygonal shapes of the cells are also envisioned in some other embodiments. Alternatively, in some embodiments, the lattice structure 410 is constructed from a single tube of Nitinol that is laser cut (to form the cells) and shape-set in the depicted shape. The lattice structure 410 defines a circular opening at each end of the IMRD 400.

The lattice structure 410 also shows great elasticity under stress. Accordingly, the IMRD 400 can be radially compressed to a very low profile for transcatheter delivery to the ventricle 200. The lattice structure 410 can be expanded to the illustrated configuration when it emerges from a delivery sheath/catheter.

In some embodiments, the lattice structure 410 is a network of thin strips of fabric created from a single fabric sheet. The thin strips of fabric can be contoured similarly to the inner surface of the ventricle 200. The strips of fabric are shown in a vertical-horizontal (circumferential) configuration but can be configured in other patterns incorporating diagonals.

The lattice structure 410 can include various types of physical features for anchoring the IMRD 400 to the ventricle 200, and to thereby provide migration resistance. For example, in the depicted embodiment the lattice structure 410 includes integrated attachment barbs 412 made of Nitinol that are used to secure the IMRD 400 within the wall of the ventricle 200. In some cases, the attachment barbs 412 are inserted into the heart wall during initial the insertion of the IMRD 400 within the ventricle 200. The attachment barbs 412 can induce heart wall tissue ingrowth, for additional securing and migration resistance.

In some embodiments, the lattice structure 410 incorporates the attachment barbs 412 at each strip-to-strip intersection point. The attachment barbs 412 can extend barb-first through openings at each strip-to-strip intersection point of the lattice structure 410. The attachment barbs 412 can be joined to the lattice structure 410 with a polymeric adhesive coating. The lattice structure 410 can take the load from the attachment barbs 412 and pull taut as the attachment barbs 412 travel outward with ventricle diastole.

Figure 14:
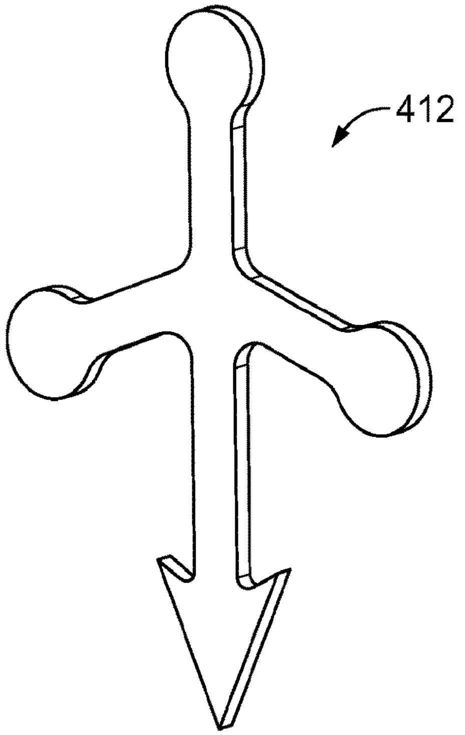
FIGS. 14-16 illustrate various example configurations of attachment barbs that can be used with any of the implantable intraventricular tensile myocardial recovery devices described herein.
Figure 15:
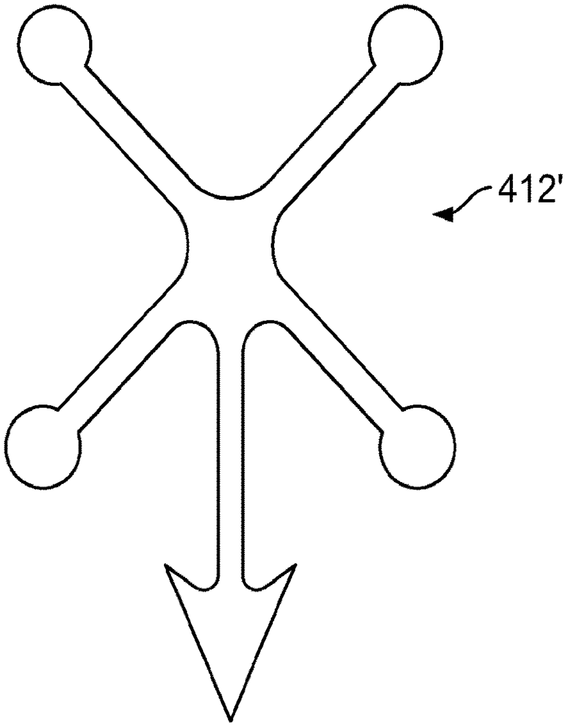

FIGS. 14 and 15 depict example types of attachment barbs 412 and 412' that can be used with the IMRD described herein (e.g., the IMRD 400). The attachment barbs 412 and 412' can be made of Nitinol (like the lattice structure 410). In some embodiments, the attachment barbs 412 and 412' can be attached to the lattice structure 410 by laser welding.

The attachment barbs 412 and 412' can be attached to the lattice structure 410 on either the inside or the outside of the lattice structure 410. In cases in which the attachment barbs 412 and 412' are attached to the inside of the lattice structure 410, the barbed portion of the attachment barbs 412 and 412' can extend radially outward through an opening in the wall of the lattice structure 410. The attachment barbs 412 and 412' can be oriented to point either upward (as shown), downward, or a combination of both upward and downward.

Figure 16:
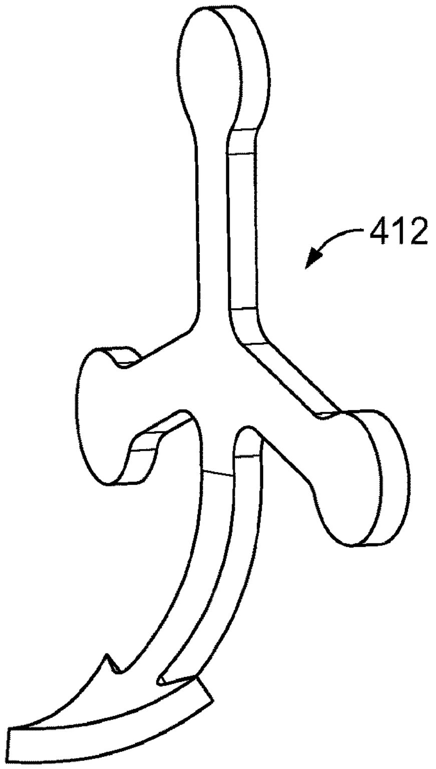

Referring to FIG. 16, in some embodiments the attachment barbs 412 and 412' can have shape memory properties. Accordingly, when heated to body temperature (such as soon after deployment into the heart) the barbed portion of the attachment barbs 412 and 412' can reconfigure to the shape shown in FIG. 16. Accordingly, the attachment barbs 412 and 412' can become inserted into the heart wall during initial the insertion of the IMRD 400 within the ventricle 200. The attachment barbs 412 and 412' can also induce heart wall tissue ingrowth, for additional securing and migration resistance.

Figure 17:
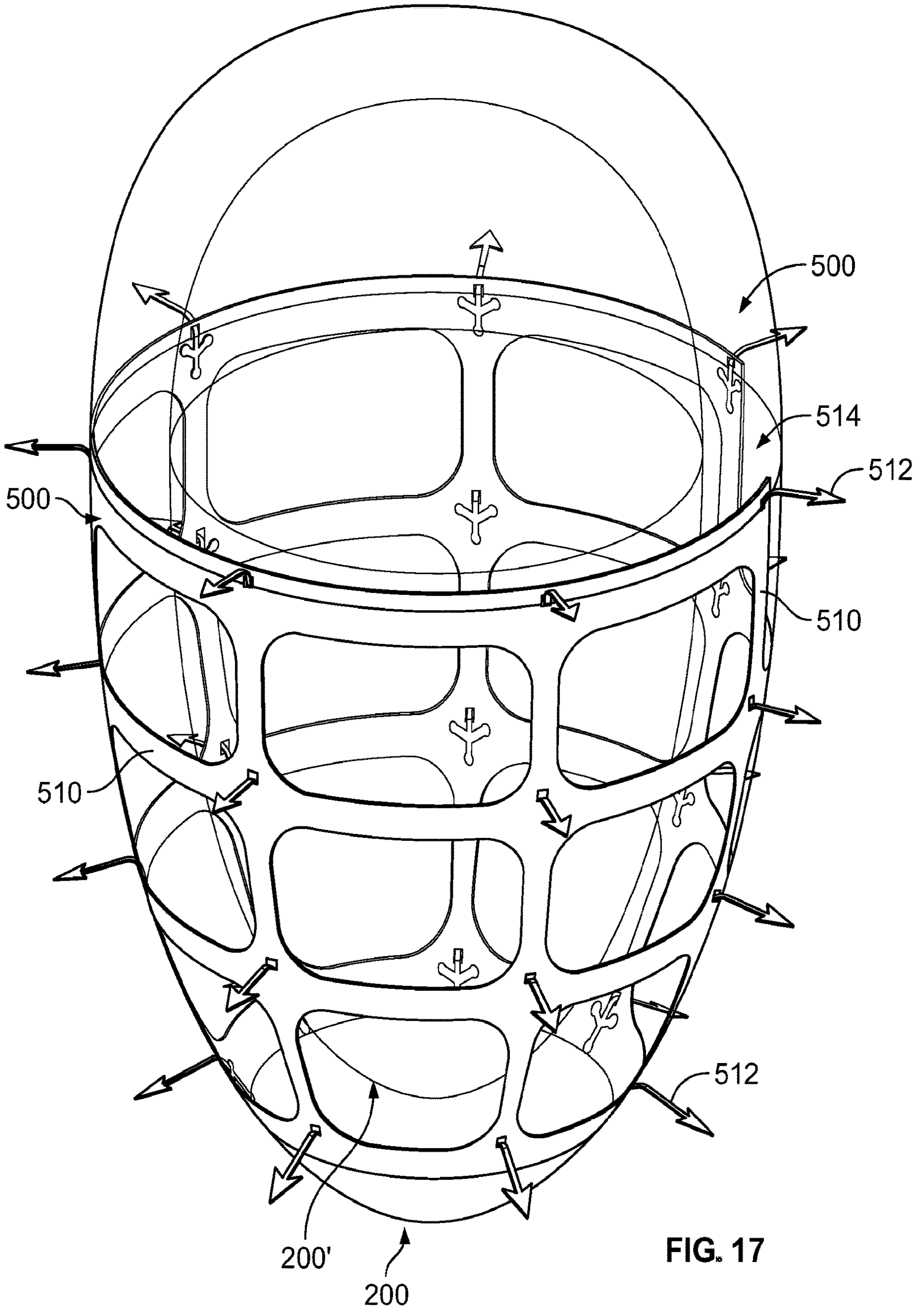
FIG. 17 is an enlarged view of another example implantable intraventricular tensile myocardial recovery device within a schematically represented ventricle.

FIG. 17 depicts another example type of IMRD 500 that is implanted within the ventricle 200. This illustration also shows the ventricle 200' which is in the contracted state.

The IMRD 500 is shorter in length that the IMRD 400. For example, in some embodiments the IMRD 400 is about 79 mm in length during diastole, whereas the IMRD 500 is about 58 mm in length during diastole.

The IMRD 500 includes a lattice structure 510. The lattice structure 510 is a flexible structure that limits the expansion of the left ventricle 200 to prevent over-expansion. Additionally, the lattice structure 510 augments patient's heart by storing energy during heart expansion (diastole) and releasing stored energy during heart contraction (systole). The lattice structure 410 can collapse freely during systole. The lattice structure 510 is designed to flex for the lifetime of the patient (e.g., billions of cycles).

In some embodiments, the lattice structure 510 is comprised of a fabric material such as, but not limited to, polyester. For example, in some embodiments the fabric material is polyester configured in a woven or knit construction. One of the benefits provided by using such a fabric as a material of the lattice structure 510 is fatigue resistance. That is, in some embodiments the lattice structure 510 comprised of a fabric material will last longer than other types of materials.

The lattice structure 510 is comprised of multiple rectangular cells that arranged into a generally cylindrical or frustoconical shape. Other polygonal shapes of the cells are also envisioned in some other embodiments. Alternatively, in some embodiments the lattice structure 510 is constructed from a single tube of Nitinol that is laser cut (to form the cells) and shape-set in the depicted shape.

The lattice structure 510 includes an open U-shaped cell 514. Here, one side of the typical rectangular cell is missing. Accordingly, the U-shaped cell 514 has three sides and an open top. In some embodiments, the open U-shaped cell 514 can advantageously accommodate (e.g., provide clearance space for) papillary muscles and/or chordae tendineae. In some embodiments, the lattice structure 510 can have a single open U-shaped cell 514 (as shown). Alternatively, in some embodiments the lattice structure 510 can have two or more open U-shaped cells 514.

The lattice structure 510 exhibits great elasticity under stress. Accordingly, the IMRD 500 can be radially compressed to a very low profile for transcatheter delivery to the ventricle 200. The lattice structure 510 can be expanded to the illustrated configuration when it emerges from a delivery sheath/catheter.

In some embodiments, the lattice structure 510 is a network of thin strips of fabric created from a single fabric sheet. The thin strips of fabric can be contoured similarly to the inner surface of the ventricle 200. The strips of fabric are shown in a vertical-horizontal (circumferential) configuration but can be configured in other patterns incorporating diagonals.

The lattice structure 510 can include various types of physical features for anchoring the IMRD 500 to the ventricle 200, and to thereby provide migration resistance. For example, in the depicted embodiment the lattice structure 510 includes integrated attachment barbs 512 made of Nitinol that are used to secure the IMRD 500 within the wall of the ventricle 200. In some cases, the attachment barbs 512 are inserted into the heart wall during initial the insertion of the IMRD 500 within the ventricle 200. The attachment barbs 512 can induce heart wall tissue ingrowth, for additional securing and migration resistance.

In some embodiments, the lattice structure 510 incorporates the attachment barbs 512 at each strip-to-strip intersection point. The attachment barbs 512 can extend barb-first through openings at each strip-to-strip intersection point of the lattice structure 510. The attachment barbs 512 can be joined to the lattice structure 510 with a polymeric adhesive coating. The lattice structure 510 can take the load from the attachment barbs 512 and pull taut as the attachment barbs 512 travel outward with ventricle diastole.

The IMRDs described herein are scalable to be usable in any size of heart. For example, in a preferred embodiment, the size of the top opening of the IMRDs is about 53 mm to 58 mm during diastole and about 38 mm to 44 mm during systole.

Figure 18:
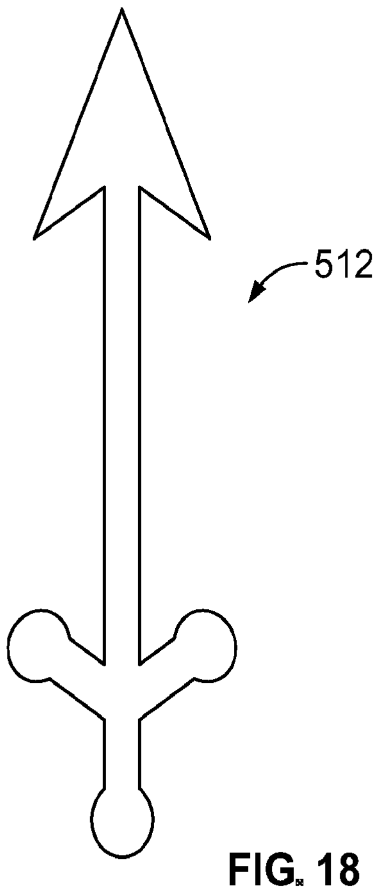
FIGS. 18-23 illustrate additional example configurations of attachment barbs that can be used with any of the implantable intraventricular tensile myocardial recovery devices described herein.

FIG. 18 shows the attachment barb 512 in isolation from the framework 510. The attachment barb 512 can be made of Nitinol (like the framework 510). In some embodiments, the attachment barb 512 can be attached to the framework 510 by laser welding.

The attachment barb 512 can be attached to the framework 510 on either the inside or the outside of the framework 510. In cases in which the attachment barb 512 is attached to the inside of the framework 510, the barbed portion of the attachment barb 512 can extend radially outward through an opening in the wall of the framework 510. The attachment barbs 512 on the framework 510 can be oriented to point either upward, downward (as shown), or a combination of both upward and downward.

Figure 19:
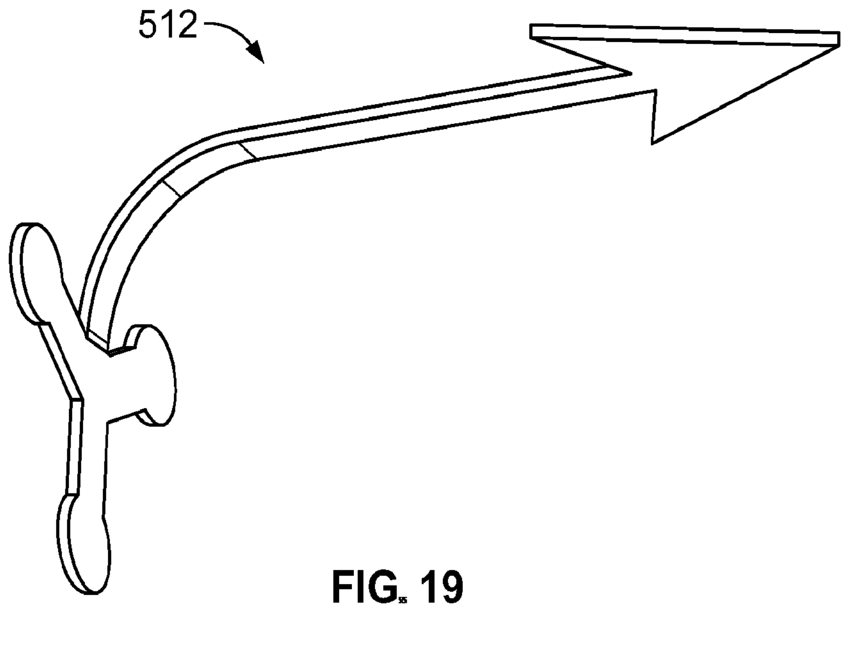

Referring to FIG. 19, in some embodiments the attachment barbs 512 can have shape memory properties. Accordingly, when heated to body temperature (such as soon after deployment into the heart) the barbed portion of the attachment barb 512 can reconfigure to the shape shown in FIG. 19. Accordingly, the attachment barbs 512 can become inserted into the heart wall during initial the insertion of the IMRD 500 within the ventricle 200. The attachment barbs 512 can also induce heart wall tissue ingrowth, for additional securing and migration resistance.

FIGS. 20-23 show additional views of some of the types of attachment features that can be used with the IMRDs described herein. The attachment features are saleable to any suitable sizes (length, width, thickness, etc).

Figure 20:
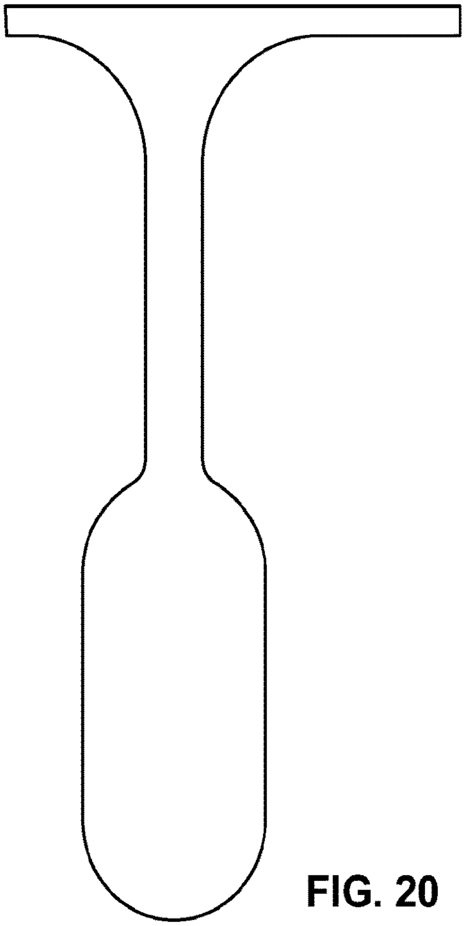
Figure 21:
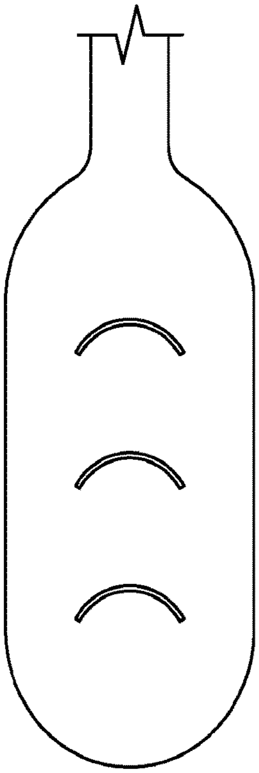

FIGS. 20 and 21 show variations of tines that can be used, for example, as the attachment barbs 312 (FIG. 12). As shown in FIG. 21, in some embodiments the tines can have one or more openings through which tissue ingrowth can take place.

Figure 22:
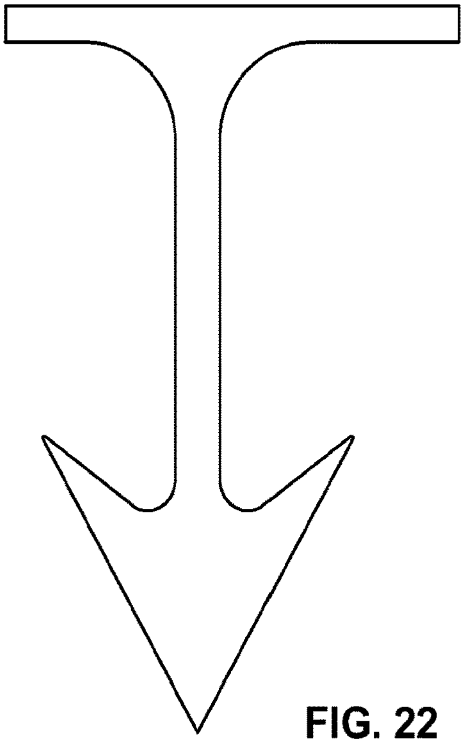
Figure 23:
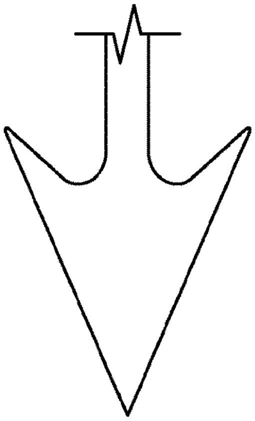

FIGS. 22 and 23 show variations of barbs that can be used, for example, as the attachment barbs 412 (FIG. 13) or the attachment barbs 512 (FIG. 17). The angles and proportions of the arrowheads of the barbs can be made/selected to attain any suitable geometries.

Example Deployment Techniques

In some embodiments, the IMRDs described herein are elastically self-expandable to the deployed configurations shown in the figures. Shape-memory is also used in some cases.

Alternatively, in some embodiments the IMRDs described herein are deployed by fully expanding (or partially expanding) the framework using one or more balloons that are inflated inside of the framework to expand the IMRD. Such balloons can have various expanded shapes (e.g., cylindrical, conical, square, dog bone, offset, stepped, etc.).

In some embodiments, the expanded diameter of the balloon is equal to the inside diameter of the fully expanded framework of the IMRD. Accordingly, the framework of the IMRD can be fully expanded simply by expanding the balloon.

Alternatively, in some embodiments the balloon used for expanding the framework of the IMRD is smaller in diameter than the inside diameter of the fully expanded framework of the IMRD. In such a case, the expanded balloon can be moved around within the inside of the framework of the IMRD to incrementally expand the framework. Various techniques for moving then balloon around within the inside of the framework can be used. For example, in some embodiments the balloon can be rolled around the inside of the framework. In other cases, the balloon can be manipulated to push outwardly at various locations on inside of the framework (such as at the nodes of the framework). When using the balloon to push outwardly at various locations on inside of the framework, in some cases the balloon can be manipulated around in the inside of the framework in a star pattern to ensure even expansion and attachment around the ventricle.

Example Radially Compressed Deployment Configurations

In some embodiments, the IMRDs described herein can be deployed using non-invasive or minimally invasive transcatheter techniques. FIGS. 24-27 depict various example configurations by which the IMRDs described herein can be radially compressed and contained within a delivery sheath/catheter.

Figure 24:
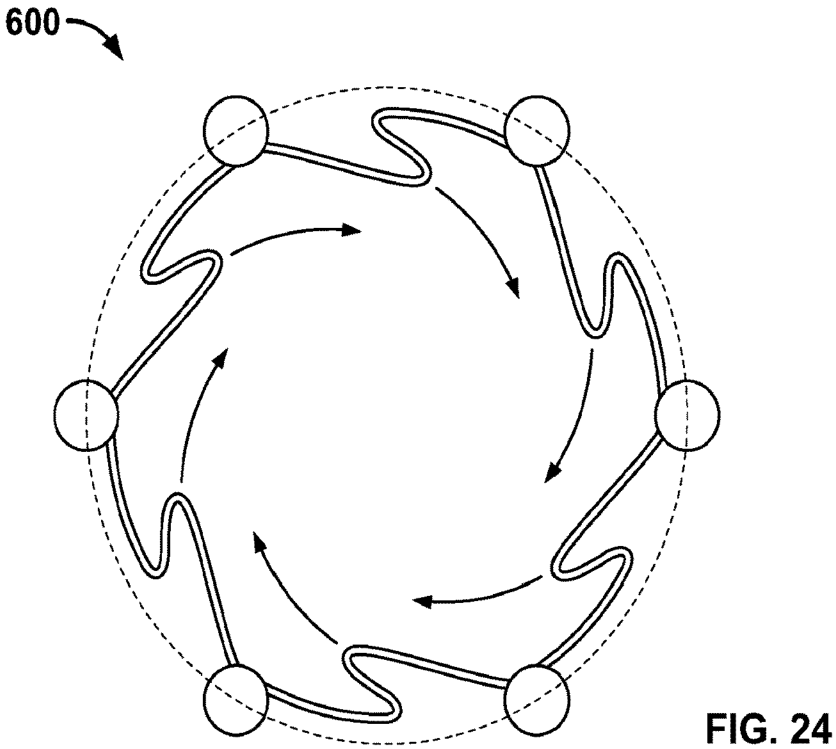
FIGS. 24-27 depict various example configurations by which the implantable intraventricular tensile myocardial recovery devices described herein can be radially compressed and contained within a delivery sheath/catheter.

In the example of FIG. 24, an example IMRD 600 (which is representative of any of the IMRDs described herein) is radially compressed in a first circular pleating arrangement. In this first circular pleating arrangement, the attachment points are on the outside diameter of the IMRD 600 while it is in the low-profile delivery configuration (as shown).

Figure 25:
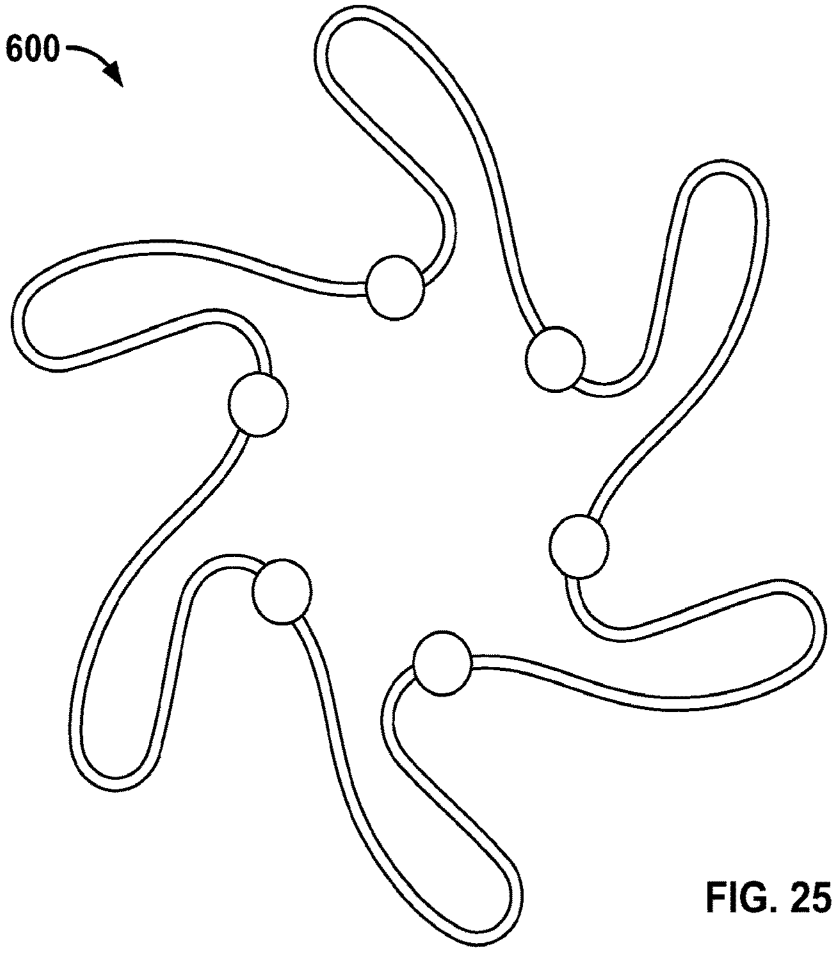

In the example of FIG. 25, the example IMRD 600 is radially compressed in a second circular pleating arrangement. In this second circular pleating arrangement, the attachment points are on the inside of the IMRD 600 while it is in the low-profile delivery configuration (as shown). This arrangement provides a smoother outer surface than the first circular pleating arrangement.

Figure 26:
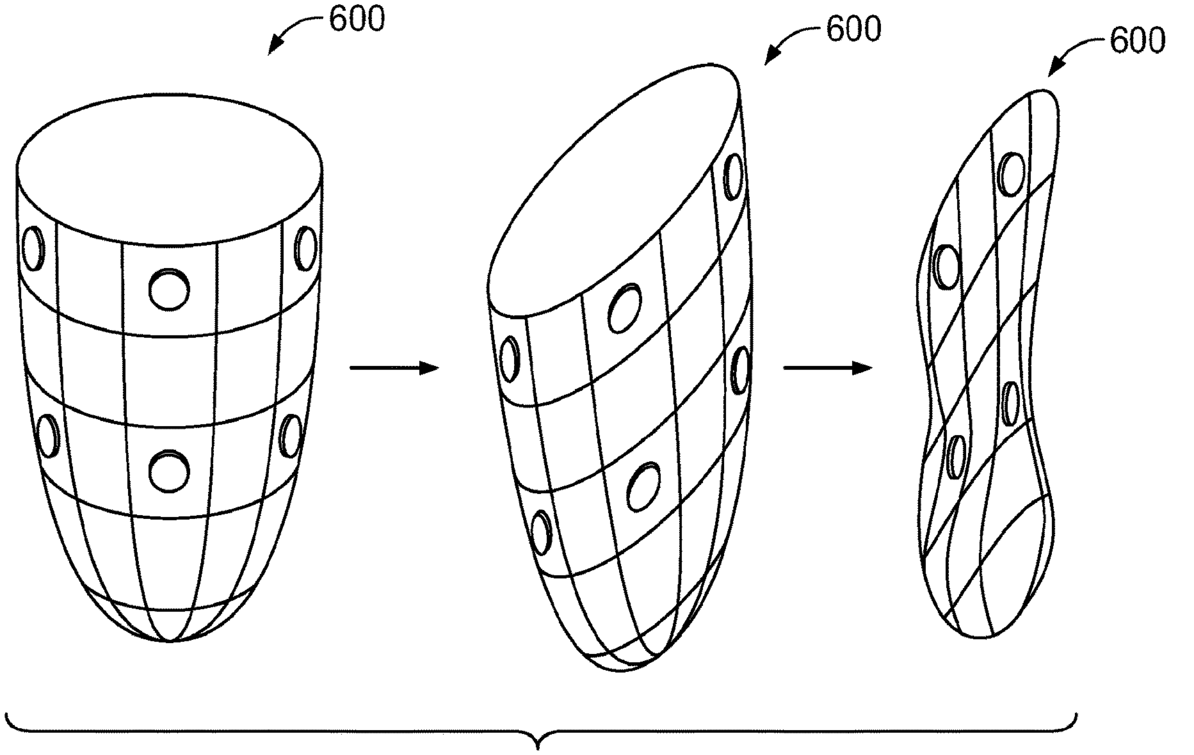

In the example of FIG. 26, the example IMRD 600 is spirally twisted to a low profile deployment arrangement.

Figure 27:
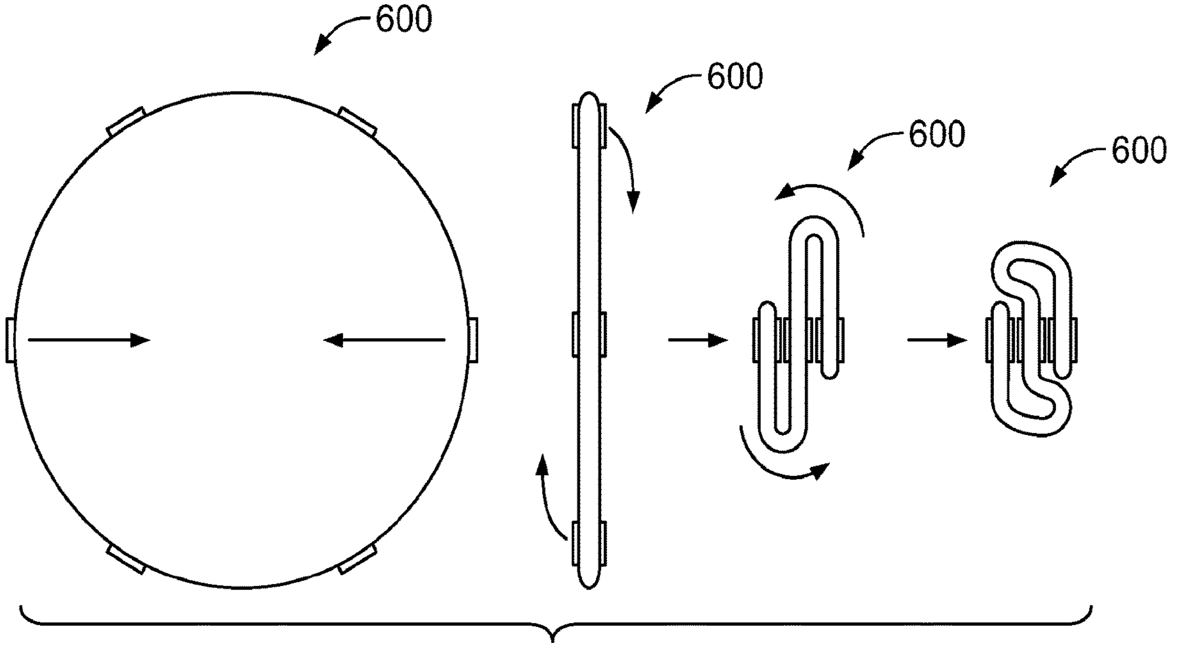

In the example of FIG. 27, the example IMRD 600 is folded (and twisted in some cases) to a low profile deployment arrangement.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. An intraventricular implantable device configured to augment cardiac function, the device comprising a framework comprising:

multiple elongate fabric elements arranged in a conical shape that defines a central longitudinal axis, the multiple elongate fabric elements including multiple longitudinally-extending fabric elements extending toward an apex of the conical shape; and multiple Nitinol attachment barbs extending from the multiple elongate fabric elements, wherein the framework is sized to reside against an inner wall of a ventricle of a human heart, and wherein the multiple Nitinol attachment barbs extend through openings at strip-to-strip intersections of the multiple elongate fabric elements.

2. The device of claim 1, wherein the framework comprises multiple rectangular cells defined by the multiple elongate fabric elements.

3. The device of claim 2, wherein the framework comprises at least one U-shaped cell with an open side.

4. The device of claim 1, wherein the framework defines a circular opening at each end of the intraventricular implantable device.

5. A method of treating heart failure of a patient, the method comprising:

implanting the device of claim 1 in a ventricle of the patient.

6. The method of claim 5, wherein the ventricle is a right ventricle.

7. The method of claim 5, wherein the ventricle is a left ventricle.

8. The device of claim 1, wherein the multiple elongate fabric elements comprise a network of thin strips of fabric created from a single fabric sheet.

9. The device of claim 1, wherein the multiple Nitinol attachment barbs are oriented to point either upward, downward, or a combination of both upward and downward relative to the central longitudinal axis.

10. The device of claim 1, wherein the framework comprises an open U-shaped cell having a single open U-shaped cell providing clearance space for papillary muscles or chordae tendineae.

11. An intraventricular implantable device configured to augment cardiac function, the device comprising:

a framework comprising:

multiple elongate fabric elements arranged in a conical shape that defines a central longitudinal axis, the multiple elongate fabric elements including multiple longitudinally-extending fabric elements extending toward an apex of the conical shape; and multiple Nitinol attachment barbs extending from the multiple elongate fabric elements, wherein the framework is sized to reside against an inner wall of a ventricle of a human heart, and wherein the multiple Nitinol attachment barbs are joined to the framework with a polymeric adhesive coating.

12. The device of claim 11, wherein the framework comprises multiple rectangular cells defined by the multiple elongate fabric elements.

13. The device of claim 12, wherein the framework comprises at least one U-shaped cell with an open side.

14. The device of claim 11, wherein the framework defines a circular opening at each end of the intraventricular implantable device.

15. A method of treating heart failure of a patient, the method comprising:

implanting the device of claim 11 in a ventricle of the patient.

16. The method of claim 15, wherein the ventricle is a right ventricle.

17. The method of claim 15, wherein the ventricle is a left ventricle.

18. The device of claim 11, wherein the multiple elongate fabric elements comprise a network of thin strips of fabric created from a single fabric sheet.

19. The device of claim 11, wherein the multiple Nitinol attachment barbs are oriented to point either upward, downward, or a combination of both upward and downward relative to the central longitudinal axis.

20. The device of claim 11, wherein the framework comprises an open U-shaped cell having a single open U-shaped cell providing clearance space for papillary muscles or chordae tendineae.

* * * * *